(12) United States Patent
Kawakami et al.

(10) Patent No.: US 7,967,802 B2
(45) Date of Patent: *Jun. 28, 2011

(54) BREAST MILK ABSORBENT PAD

(75) Inventors: Hikari Kawakami, Kagawa-ken (JP); Michiyo Fujikawa, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 518 days.

This patent is subject to a terminal disclaimer.

(21) Appl. No.: 11/936,993

(22) Filed: Nov. 8, 2007

(65) Prior Publication Data

US 2008/0140040 A1 Jun. 12, 2008

(30) Foreign Application Priority Data

Nov. 9, 2006 (JP) .................................. 2006-304268

(51) Int. Cl.
*A61F 13/15* (2006.01)
(52) U.S. Cl. ........ 604/385.07; 604/385.02; 604/385.201
(58) Field of Classification Search ............. 604/385.02, 604/385.07, 385.201
See application file for complete search history.

(56) References Cited

U.S. PATENT DOCUMENTS

| 4,074,721 | A | * | 2/1978 | Smits et al. | 604/366 |
| 6,039,629 | A | * | 3/2000 | Mitchell | 450/57 |
| 6,074,272 | A | * | 6/2000 | Hebert | 450/37 |
| 6,896,668 | B2 | * | 5/2005 | Kashiwagi et al. | 604/385.02 |
| 6,945,966 | B2 | * | 9/2005 | Mikami | 604/346 |
| 2007/0287977 | A1 | * | 12/2007 | Fujikawa et al. | 604/385.07 |
| 2007/0287978 | A1 | * | 12/2007 | Fujikawa et al. | 604/385.07 |
| 2008/0294136 | A1 | * | 11/2008 | Kawakami et al. | 604/385.07 |

FOREIGN PATENT DOCUMENTS

JP 2001-11704 1/2001

* cited by examiner

*Primary Examiner* — Lynne Anderson

(74) *Attorney, Agent, or Firm* — Brinks Hofer Gilson & Lione

(57) ABSTRACT

A breast milk absorbent pad includes elastically stretchable/contractible members arranged along transversely opposite side edges of the pad. Corners where one of the transversely opposite side edges and one of the longitudinally opposite end edges of a pad-chassis join are folded to a non-skin-contactable side. The breast milk absorbent pad is packed in a package with the corners folded.

7 Claims, 5 Drawing Sheets

BREAST MILK ABSORBENT PAD

CROSS-REFERENCE TO RELATED APPLICATIONS

This application is based upon and claims the benefit of priority from the prior Japanese Patent Application No. 2006-304268, filed on Nov. 9, 2006; the entire contents of which are incorporated herein by reference.

BACKGROUND OF THE INVENTION

The present invention relates generally to a breast milk absorbent pad.

Breast milk absorbent pads have conventionally been well known, which typically includes a liquid-absorbent layer and a liquid leak-barrier sheet covering the outer surface of the liquid-absorbent layer. For example, Japanese Unexamined Patent application Publication No. 2001-11704 (hereinafter referred to as "Reference 1") discloses the breast milk absorbent pad generally including a pad-chassis composed of a body fluid absorbent structure layered between a surface member and a waterproof member and a pair of elastically stretchable/contractible members respectively extending along transversely opposite side edges of the body fluid absorbent structure.

The breast milk absorbent pad disclosed in Reference 1 is advantageous in some points. For example, contractile force of the pair of stretchable/contractible members secured between the absorbent structure and the surface member can deform the breast milk absorbent pad as a whole into a dome-like shape fitted to the shape of a breast without the need of heating and pressurizing.

However, the breast milk absorbent pad disclosed in Reference 1 has also left various problems behind unsolved. For example, when the contractile force of the elastically stretchable/contractible members pulls peripheries of the pad in the direction of contraction, the contractile force causes relatively highly flexible four corners of the pad to be folded inward to a skin-contactable side where the stretchable/contractible members are attached. Such contact by the corners may create irritation and a feeling of discomfort against the skin of the wearer.

SUMMARY OF THE INVENTION

It is an object of the present invention to solve at least one of the problems in the conventional breast milk absorbent pad.

According to one aspect of the present invention, a breast milk absorbent pad having a longitudinal direction and a transverse direction and comprises: a pad-chassis including a liquid-pervious inner sheet defining a skin-contactable side, a non-liquid-pervious outer sheet defining at a non-skin-contactable side, and a body fluid absorbent core having a panel shape and interposed between the inner sheet and the outer sheet; and elastic members respectively which extend along transversely opposite sides of the pad-chassis in the longitudinal direction in a stretched state and are capable of making the pad-chassis curved in a concave shape with the skin-contact side inside under a contractile force, corners of the pad-chassis where transversely opposite side edges of the pad-chassis extending in the longitudinal direction join longitudinally opposite end edges of the pad-chassis extending in the transverse direction being folded to the non-skin-contactable side, and the breast milk absorbent pad being packed in a package with the corners in such a folded state.

According to another aspect of the present invention, a breast milk absorbent pad having a longitudinal direction and a transverse direction and comprising: a pad-chassis including a liquid-pervious inner sheet defining a skin-contactable side, a non-liquid-pervious outer sheet defining a non-skin-contactable side, and a body fluid absorbent core having a panel shape and interposed between the inner sheet and the outer sheet; means for making the pad-chassis curved in a concave shape with the skin-contactable side inside; and means for folding corners of the pad-chassis where transversely opposite side edges of the pad-chassis extending in the longitudinal direction join longitudinally opposite end edges of the pad-chassis extending in the transverse direction to the non-skin-contactable side.

Other aspects of the present invention will be explained below.

DETAILED DESCRIPTION OF THE PREFERRED EMBODIMENTS

Exemplified embodiments relating to the present invention will be fully understood from the description given hereunder with reference to the accompanying drawings.

Figure 1:
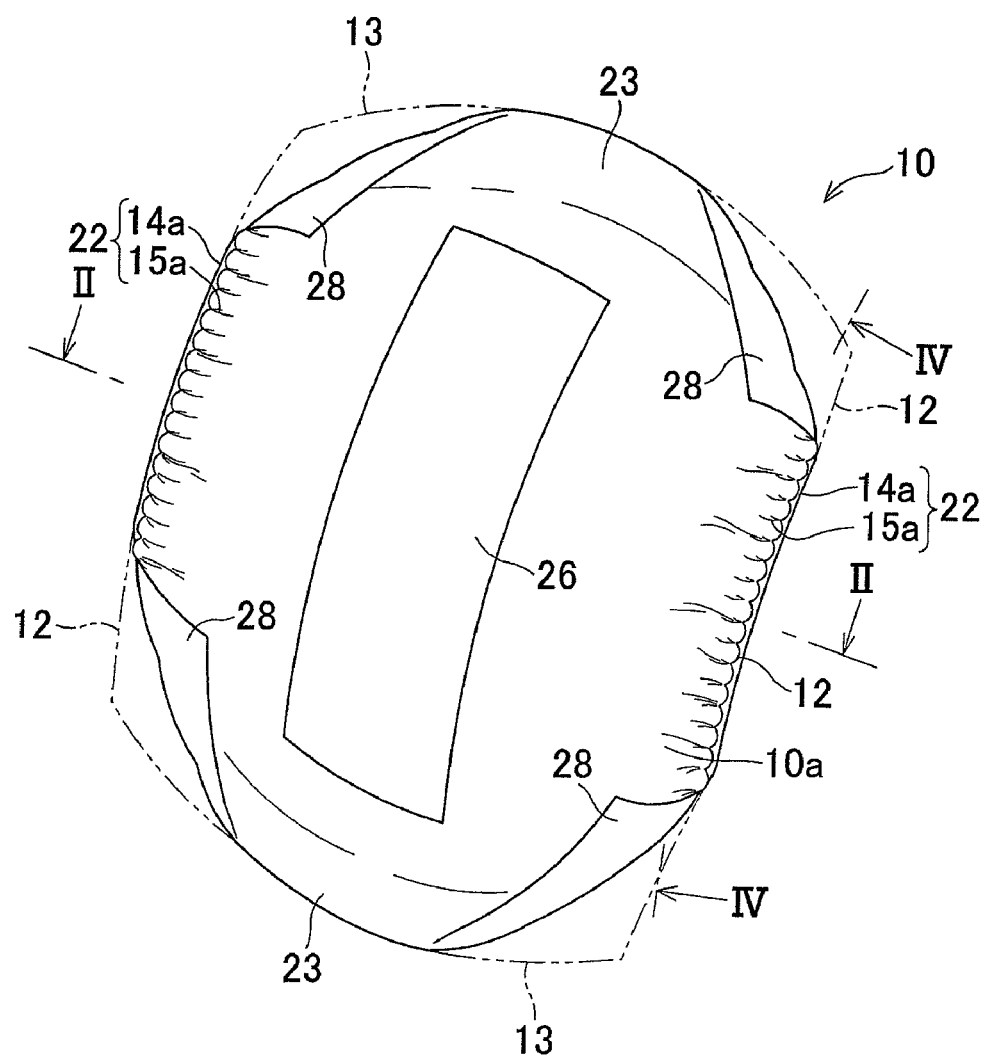
FIG. 1 is a perspective view of a breast milk absorbent pad according to one embodiment of the present invention as viewed from a non-skin-contactable side.
Figure 2:
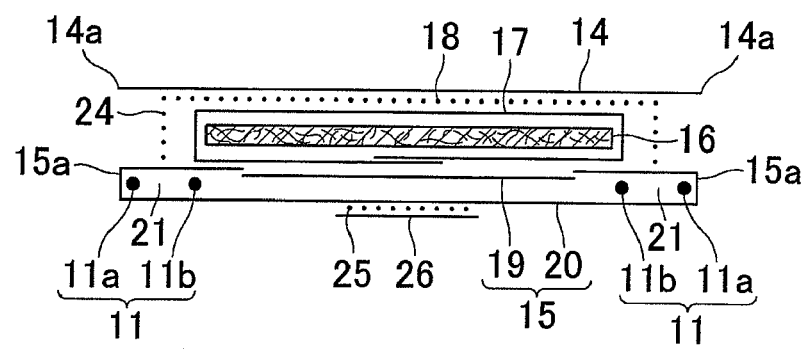
FIG. 2 is a schematic transverse sectional view taken along the line II-II in FIG. 1.

FIG. 1 is a perspective view of a breast milk absorbent pad 10 in which elastically stretchable/contractible members are contracted; FIG. 2 is a schematic sectional view taken along the line II-II in FIG. 1; and FIG. 3 is a plan view of the breast milk absorbent pad 10 in which an inner sheet 14 is removed and side portion is partially omitted.

Figure 3:
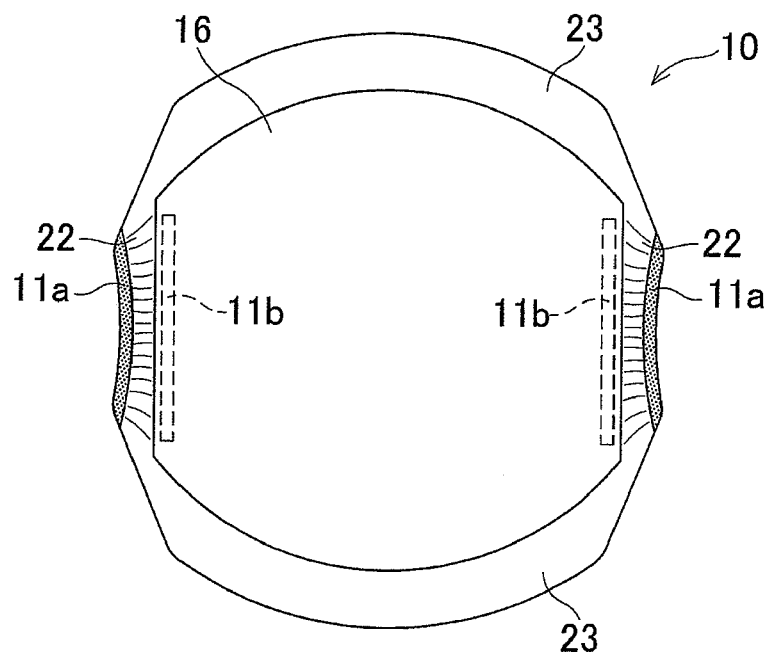
FIG. 3 is a plan view of the breast milk absorbent pad according to the embodiment in which an inner sheet and a part of a side portion are omitted.

As will be apparent from FIGS. 1, 2, and 3, the breast milk absorbent pad 10 includes a pad-chassis 10a having a longitudinal direction and a transverse direction when used, and a pair of elastically stretchable/contractible members 11. The contour of the pad-chassis 10a is defined by a pair of transversely opposite side edges 12 extending substantially parallel in the longitudinal direction, and end edges 13 extending substantially in the transverse direction in a convex shape. The pad-chassis 10a is externally shaped substantially in ellipsoid having its major axis extending in the longitudinal direction of the pad. The contour of the pad-chassis 10a in the drawings, however, is shown merely by way of example. The pad-chassis 10a can be in any appropriate shape, such as, for example, an egg shape or a heart shape.

The pad-chassis 10a includes a body fluid-pervious inner sheet 14 to define a skin-contactable side, a body fluid leak-barrier outer sheet 15 to define a non-skin-contactable side, and a body fluid absorbent core 16 interposed between these sheets. The core 16 is entirely wrapped with a body fluid-spreadable shape retaining sheet 17. The core 16 wrapped with the shape retaining sheet 17 is intermittently bonded to the inner surface of the inner sheet 14 with hot melt adhesive 18.

The outer sheet 15 includes an inner layer 19 underlying the core 16, and an outer layer 20 extending outward beyond the outer peripheries of the inner layer 19. The inner layer 19 and the outer layer 20 are bonded together by means of hot melt adhesives (not shown) along the transversely opposite edges of the inner layer 19. Side portions of the outer layer 20 are folded back inwardly of the pad-chassis 10a to form sleeves 21. Laterally extending portions (hereinafter referred to as extension portions 15a of the outer sheet 15) extend outward beyond the transversely opposite side edges of the core 16 by substantially the same dimension as extension portions 14a of the inner sheet 14. The transversely opposite side edges, i.e., extension portions 14a of the inner sheet 14 may extend further outward from the extension portions 15a of the outer sheet 15 if appropriate.

The pad-chassis 10a includes side flaps 22 respectively extending outward in the transverse direction from the transversely opposite side edges of the core 16 and extending in the longitudinal direction to define the side edges 12, and end flaps 23 extending outward in the longitudinal direction from the longitudinally opposite end edges of the core 16 and extending in the transverse direction to define the end edges 13. Each side flap 22 is defined by the extension portion 14a of the inner sheet 14 and the extension portion 15a of the outer sheet 15. The extension portions 14a, 15a are bonded to each other with hot melt adhesive 24 applied at positions respectively spaced from the outermost side edges of the extension portions 14a, 15a inward of the pad-chassis 10a. Therefore, the extension portions 14a, 15a are separated from each other along the outermost side edges thereof.

The elastically stretchable/contractible members 11 are respectively arranged along the side flaps 22, and each includes first and second elastically stretchable/contractible members 11a, 11b. Specifically, the first elastically stretchable/contractible members 11a extend respectively along the extension portions 15a of the outer sheet 15 in the longitudinal direction, while the second elastically stretchable/contractible members 11b extend respectively along the transversely opposite side edges of the core 16 in the longitudinal direction spaced from and parallel to the first elastically stretchable/contractible members 11a. The first and second elastically stretchable/contractible members 11a, 11b are attached in a longitudinally stretched state.

Since the second elastically stretchable/contractible members 11b are fixed along the transversely opposite side edges of the core 16, a contractile force thereof deforms a region of the pad-chassis 10a including the core 16, i.e., a region with the highest rigidity in the pad-chassis 10a, together with the side flaps 22, so that the pad-chassis 10a as a whole is concavely curved with the inner sheet 14 at a skin-contactable side inside. Thus, the pad 10 deforms into a cup-like shape fitted to the shape of the breast of the wearer. The first elastically stretchable/contractible members 11a fixed to the sleeves 21 of the side flaps 22 can also exert a contractile force to help deform the pad-chassis 10a.

The extension portions 14a of the inner sheet 14 are not directly affected by the contractile force of the elastically stretchable/contractible members 11, and therefore would not form undesirable gathers to leave compression marks on the wearer's skin or create a feeling of discomfort against the skin.

On the outer surface of the outer sheet 15, a pressure-sensitive adhesive 25 and a separator 26 extend at a widthwise central portion in the longitudinal direction. The pressure-sensitive adhesive 25 adheres to the brassiere or other wearing article to prevent the breast milk absorbent pad 10 from falling off. The separator 26 covers the pressure-sensitive adhesive 25.

Figure 4:
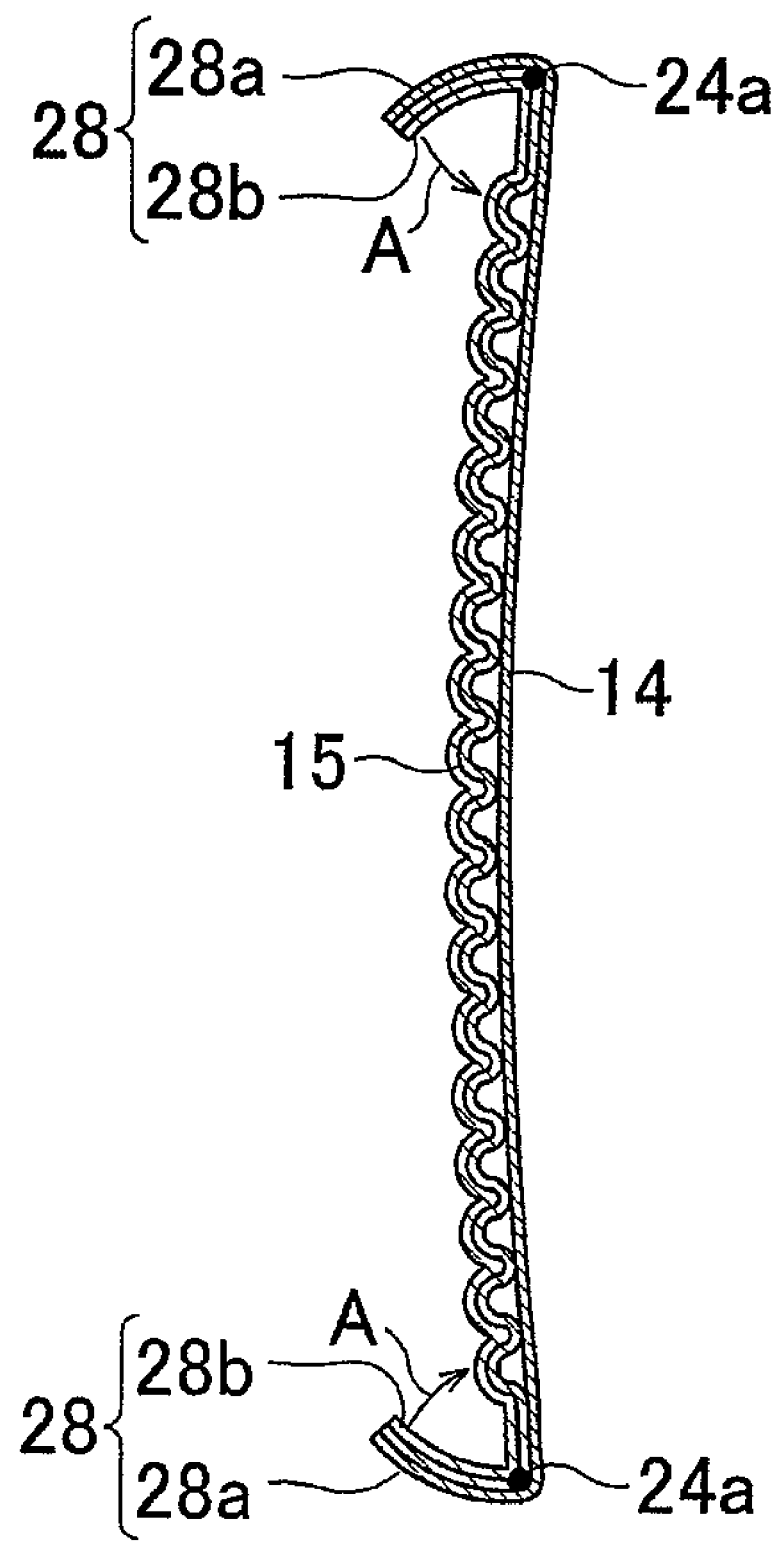
FIG. 4 is a longitudinal sectional view taken along the line IV-IV in FIG. 1.
Figure 5:
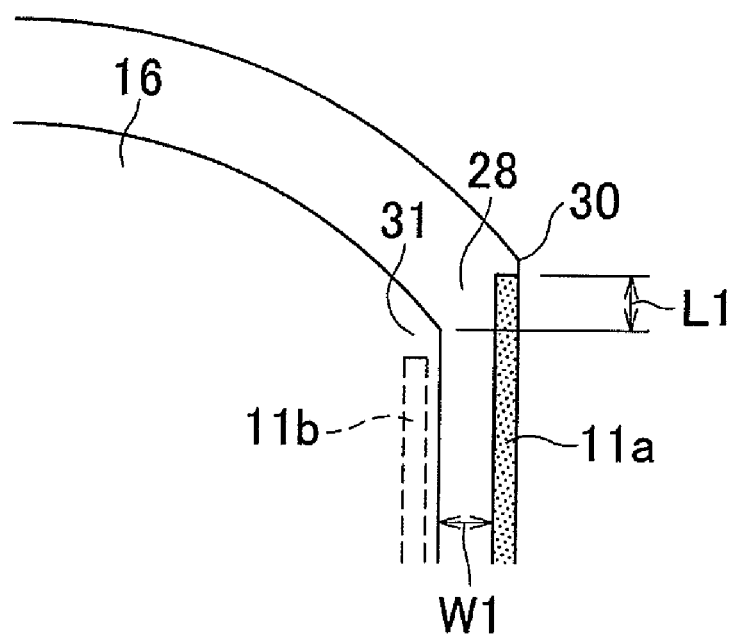
FIG. 5 is an enlarged partial plan view showing an arrangement of a first elastically stretchable/contractible member according to the embodiment.
Figure 6:
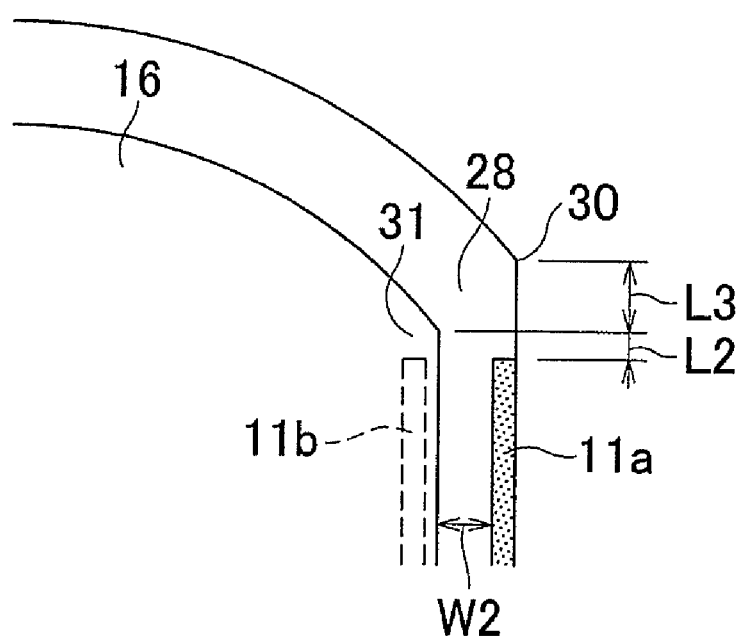
FIG. 6 is an enlarged partial plan view showing another arrangement of the first elastically stretchable/contractible member.

FIG. 4 is a longitudinal sectional view taken along the line IV-IV in FIG. 1; FIG. 5 is an enlarged partial plan view of the breast milk absorbent pad 10 in which a part of the inner sheet 14 and the side portion thereof are not shown to reveal an arrangement of the first elastically stretchable/contractible member 11a; and FIG. 6 is an enlarged partial plan view similar to FIG. 5 of an alternative embodiment of FIG. 5.

Corners 28 of the pad-chassis 10a where the side flap 22 joins the end flap 23 are folded outward of the outer sheet 15 (see FIG. 1). This is because the contractile force of the first elastically stretchable/contractible member 11a (see FIG. 3) pulls the corners 28 of the pad-chassis 10a in an outward direction (indicated by an arrow A). Specifically, with the contraction of the first elastically stretchable/contractible members 11a, the longitudinal dimension of the extension portions of the outer sheet 15, on which the first elastically stretchable/contractible members 11a are arranged, are shortened. The contractile force works inwardly along the folding boundaries defined by bonding sites 24a where the inner sheet 14 and the outer sheet 15 are bonded to each other. The contractile force pulls the flap portions 28a that extend outward from the bonding sites 24a in the inner sheet 14 toward the transversely opposite side edges of the inner sheet 14. As a result, the flap portions 28a lean against and are folded outward (in other words, bent or warped outward; when the expression "folded outward" is used hereinbelow, it connotes the same) together with the flap portions 28b of the outer sheet 15 which oppose to the transversely opposite side edges of the inner sheet 14. When the corners 28 of the pad-chassis 10a are folded outward at the bonding sites 24a of the inner sheet 14, the outer sheet 15, even such a force is applied to a portion of the end flap 23 inward beyond the bonding site 24a so that the portion might be bent outward, the vicinity of corner 31 of the core 16 would not be bent outward. This is because the region of the core 16 has a relatively high rigidity, which suppresses the contracting effect of the first elastically stretchable/contractible member 11a on the end flaps 23.

Thus, the corners 28 of the pad-chassis 10a are folded outward and not brought into direct contact with the skin of the wearer. Therefore, cut edges 30 of the corners 28 of the pad-chassis 10a are prevented from touching the skin and thereby causing a skin itching and a skin rash as well as a feeling of discomfort against skin.

In FIG. 5, the end portion of the first elastically stretchable/contractible member 11a extends outward beyond the corner 31 of the core 16 in the longitudinal direction. In the embodiment, a widthwise distance W1 between the core 16 and the first elastically stretchable/contractible member 11a is preferably in a range of 1 to 20 mm, and more preferably in a range of 2 to 10 mm so that the corner 28 of the breast milk absorbent pad-chassis 10a is folded outward by the contractile force of the first elastically stretchable/contractible member 11a.

Further, a longitudinal distance L1 between the corner 31 of the core 16 and the end portion of the first elastically stretchable/contractible member 11a is preferably in a range of 1 to 20 mm, and more preferably in a range of 5 to 15 mm.

In this case, since the first elastically stretchable/contractible member 11a extends further outward in the longitudinal direction from the edge of the core 16, the end portion of the first elastically stretchable/contractible member 11a is folded outward by its own contracting effect together with the end flap 23.

In FIG. 6, the end portion of the first elastically stretchable/contractible member 11a is placed inward of the corner 31 of the core 16 in the longitudinal direction. In this embodiment, in order to make the corner 28 of the pad-chassis 10a folded outward under the contractile force of the first elastically stretchable/contractible member 11a, a widthwise distance W2 between the core 16 and the first elastically stretchable/contractible member 11a is preferably in a range of 1 to 20 mm, and more preferably in a range of 2 to 10 mm, and a longitudinal distance L2 between the end portion of the first elastically stretchable/contractible member 11a and the corner 31 of the core 16 is preferably in a range of 1 to 10 mm, and more preferably in a range of 2 to 5 mm. Further, a longitudinal distance L3 between the corner 31 of the core 16 and the corner 28 of the pad-chassis 10a can be preferably in a range of 1 to 20 mm, and more preferably in a range of 2 to 10 mm. In this case, the end portion of the first elastically stretchable/contractible member 11a is placed longitudinally inward of the corner 31 of the core 16. Therefore, the first elastically stretchable/contractible member 11a is not folded outward together with the end flap 23 by its own contractile force by a large degree. Only a tip portion and its surrounding area of the corner 28 of the pad-chassis 10a are folded outward.

Numerical values cited above may vary depending on the contractile force of the first elastically stretchable/contractible member 11a and the rigidity of the core 16, and the inner and outer sheets 14, 15. These members are supposed to be manufactured from known materials generally used in absorbent articles such as breast milk absorbent pads, sanitary napkins, and disposable diapers of similar types.

In the embodiments shown in FIGS. 5 and 6, the end portion of the second elastically stretchable/contractible member 11b is positioned inboard of the corner 31 of the core 16. Alternatively, however, the second elastically stretchable/contractible member 11b may extend longitudinally outward of the edge of the core 16. In other words, the second elastically stretchable/contractible member 11b may extend to the end flap 23. In this case, the second elastically stretchable/contractible member 11b works in conjunction with the first elastically stretchable/contractible member 11a to exert a force to fold the corners 28 of the pad-chassis 10a outward, whereby the corners 28 of the pad-chassis 10a are more securely folded outward.

When the corner 28 of the pad-chassis 10a is folded outward, a fold line is formed in the pad-chassis 10a and contacts the skin, whereby the cut edge does not contact the skin directly to cause the itchiness and rash.

In the embodiments described above, the corners 28 of the pad-chassis 10a are folded by the contractile force of the first elastically stretchable/contractible member 11a. On the other hand, it is possible to process the pad-chassis 10a so that the corners 28 are folded outward of the outer sheet 15 no matter whether there is a contractile force of the first elastically stretchable/contractible member 11a or not. In this case, the extension portion 14a of the inner sheet 14 and the extension portion 15a of the outer sheet 15 forming the side flap 22 of the pad-chassis 10a do not need to be configured in a mutually separated manner.

Figure 7:
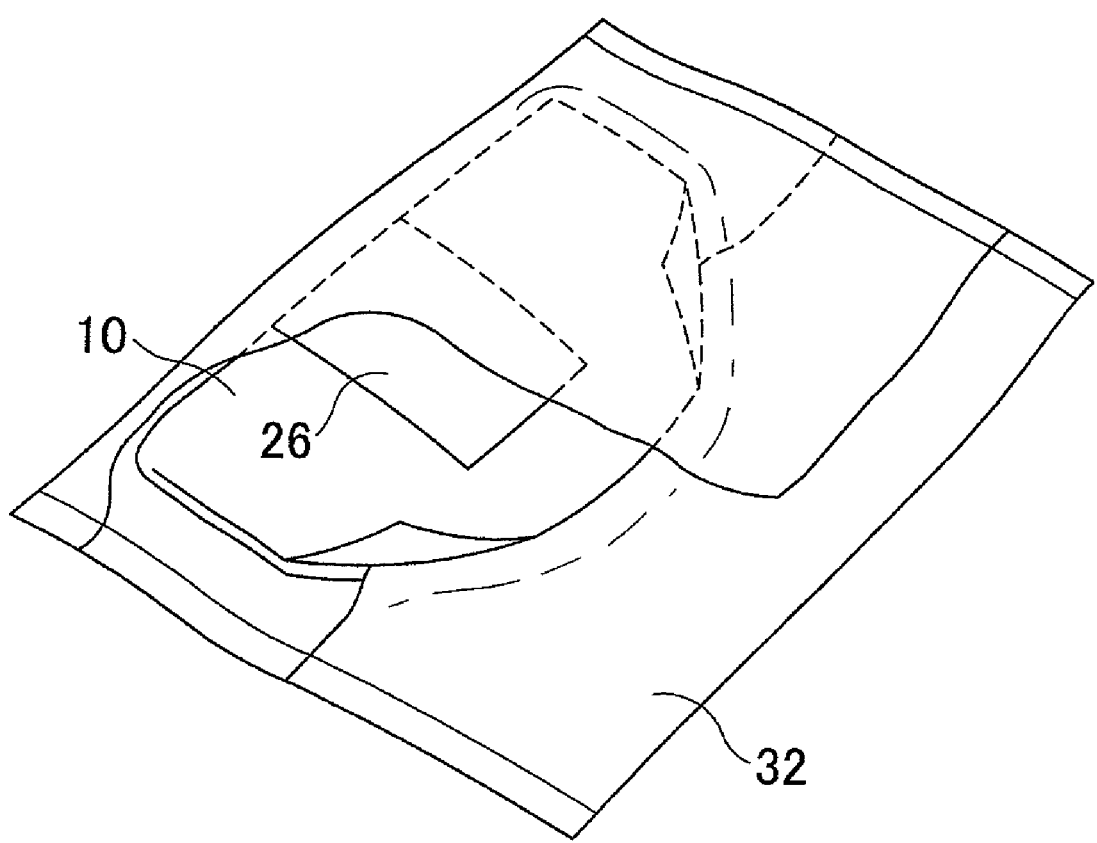
FIG. 7 is a perspective view of the breast milk absorbent pad packed in an individual package with a part of the package not shown according to the embodiment.

FIG. 7 is a perspective view of the breast milk absorbent pad 10 packed in an individual package 32 with a part of the package not shown.

When the breast milk absorbent pad 10 is folded in two along the transverse direction and packed in the individual package 32 while the corners 28 of the pad-chassis 10a remain folded outwardly, the corners 28 of the pad-chassis 10a tend to remain folded along the fold line and are not likely to return to the state before folding when used. Thus, the unprocessed cut edges of the breast milk absorbent pad or the sharp corners 28 of the pad-chassis 10a are securely prevented from touching the skin of the wearer.

The core 16 is a mixture of fluff pulp and super-absorbent polymer particles compressed to a predetermined thickness and molded into a semirigid panel of a predetermined shape. The panel preferably has a basis weight in a range of 10 to 50 $g/m^2$. The polymer particles can be starch-based, cellulose-based, or synthetic polymer-based. The body fluid-spreadable shape retaining sheet may be tissue paper or hydrophilic non-woven fabric and bonded to the core with suitable hot melt adhesives (not shown). The shape retaining sheet enhances the spreading of the body fluid, retains the shape of the core, and prevents the polymer particles from falling off.

The inner sheet 14 is a liquid-pervious sheet such as, for example, non-woven fabric or perforated plastic film, and preferably is thermoplastic non-woven fabric having a basis weight in a range of 10 to 40 $g/m^2$. The outer sheet 15 is hydrophobic non-woven fabric, non-liquid-pervious plastic film, or a laminate sheet of a hydrophobic non-woven fabric and plastic film, and preferably is a thermoplastic non-woven fabric having a basis weight in a range of 10 to 40 $g/m^2$.

Non-woven fabric used in the inner sheet 14 and the outer sheet 15 may be manufactured through spun lacing, spun bonding, thermal bonding, melt blowing, needle punching, air through, or any other appropriate method. The component fiber for non-woven fabric may be synthetic fiber, for example, olefin-based fibers such as polyethylene and polypropylene, polyether-based fibers, and polyamide-based fibers.

The elastically stretchable/contractible member 11 is preferably an elastomer such as synthetic rubber or natural rubber that stretches to 1.5 times the original length.

The bonding of the inner sheet 14 and the outer sheet 15, bonding of the core 16 thereto, and attachment of the first and the second elastically stretchable/contractible members 11a, 11b may be realized with known technique other than the use of hot melt adhesives. For example, thermal welding such as sonic sealing or heat sealing can be used.

According to the embodiments explained above, the problems in the conventional breast milk absorbent pad can be fully or at least partially solved. The exemplified problems and the exemplified effects of the embodiments will be example explained below.

In the breast milk absorbent pad disclosed in Reference 1, when the contractible force of the stretchable/contractible members pulls peripheries of the pad in the direction of contraction, relatively highly flexible four corners of the pad are folded inward to a skin-contactable side where the stretchable/contractible members are attached. In the manufacturing process of the breast milk absorbent pads of this type, a large continuous multilayered web is produced and cut into plural pads so that the pads can be supplied at reasonable cost. Therefore, a cut edge is formed in at least a part of the contour of the pad. The cut edges can create irritation and a feeling of discomfort against the skin of the wearer, particularly when the corners of the pads are sharp cut edges, or such corners are folded to the skin-contactable side. One embodiment disclosed in Reference 1 alleviates this problem by leaving end portions of the stretchable/contractible members unfixed to the pad. In this case, however, the pad may not be brought into close contact with the skin in a portion which is left loose from the stretchable/contractible members depending on the length of the portion. Then, such portion may move along the movements of the wearer to create irritation to the skin or to cause leakage of the breast milk.

To alleviate the problems caused by the sharp corners of the pad or the folded corners contacting the skin, it is possible to cut off the folded parts of the corners or to cut the corners in circular arcs, for example. Though such measures bring about a relatively advantageous effect, cut edges are left. Even when the corners are not folded or folded only slightly, the cut edges can contact the skin due to the contractile force of the elastic members. Thus the problem remains.

Further, the stretchable/contractible members fixed to the surface member which contacts the skin form a plurality of gathers due to contraction thereof. The gathers may be directly pressed against the skin to create a feeling of discomfort against or leave compression marks on the skin of the wearer.

On the other hand, according to the above embodiment of the present invention, a breast milk absorbent pad is improved so that the corners of the pad do not touch the skin of the wearer to give irritation to the skin when used, and gathers formed under a contractible force recoil of the stretchable/contractible members do not directly affect the skin.

In the breast milk absorbent pad according to the above embodiment, the corners of the pad-chassis are folded to the non-skin-contactable side so that fold lines come to the edges that contact the skin of the wearer. Thus, even when the corners are cut edges or sharp, they are not brought into contact with the skin of the wearer. Therefore, the edges of the corners do not irritate the skin of the wearer or create a feeling of discomfort.

The pad is packed with the corners folded, and thereby the corners remain folded until the pad is used. In addition, since the folded corners tend to remain in the folded shape, the corners are prevented from returning to the original shape when used or from being folded in reverse to the skin-contactable side.

In the preferred embodiment of the invention wherein the corners are located at positions where the side flap joins the end flap, and the elastically stretchable/contractible members are respectively arranged adjacent the transversely opposite side edges of the body fluid absorbent core or along the side flaps, substantially the same effect as described above can be obtained. The contraction of the elastically stretchable/contractible members does not work to make the "tendency to remain folded" disappear.

In the preferred embodiment of the invention wherein the side flap is, at an outer edge portion thereof, divided into a first portion formed from the inner sheet defining the skin-contactable side, and a second portion formed from the outer sheet defining the non-skin-contactable side opposite to the first portion, and one of the elastically stretchable/contractible member and a first elastically stretchable/contractible member separate from the elastically stretchable/contractible member is arranged along a lateral edge of the second portion, the first elastically stretchable/contractible member is arranged at the second portion of the side flap which is placed to the non-skin-contactable side. Therefore, the corners of the pad-chassis are automatically folded to the non-skin-contactable side by the contractile force of the first elastically stretchable/contractible members and remain in the folded state regardless of the presence/absence of the "tendency to remain folded". In addition, the contractile force of the first elastically stretchable/contractible member forms a plurality of gathers in the second portion while leaving the first portion, which is to the skin-contactable side, of the side flap without gathers. Therefore, no gathers are formed in the first portion to cause irritation of the skin, and the irritation of the skin by the gathers can be prevented in advance.

In the preferred embodiment of the invention wherein second elastically stretchable/contractible members are respectively attached to the second portions in a stretched state adjacent the transversely opposite edges of the body fluid absorbent core and extending parallel to the first elastically stretchable/contractible members, and at least the second elastically stretchable/contractible members among the first and second elastically stretchable/contractible members are capable of making the pad-chassis curved in a concave shape with the skin-contactable side inside, the contractible force of the second elastically stretchable/contractible members alone, or in combination with the first elastically stretchable/contractible members makes the pad-chassis curved in a concave shape with the skin-contactable side inside. In addition, the second elastically stretchable/contractible members are respectively arranged adjacent the transversely opposite side edges of the semirigid body-fluid absorbent core which is spaced apart inward at least from the peripheries of the first portions of the side flaps. Therefore, the pad-chassis is securely curved, and no gathers are formed in the second portions of the side flaps by the contraction of the second elastically stretchable/contractible members to irritate the skin.

In the preferred embodiment, wherein at least one of the end portions of the first elastically stretchable/contractible members is arranged outward of the corner of the body fluid absorbent core in the longitudinal direction, the first elastically stretchable/contractible member is folded outward together with the end flap. Therefore, a tensile stress of the outwardly-folded portion of the first elastically stretchable/contractible member serves to keep the folded state, and the folded portion rarely returns to the original state.

In the preferred embodiment, wherein at least one of the end portions of the first elastically stretchable/contractible members is arranged inward of the corner of the body fluid absorbent core in the longitudinal direction, the first elastically stretchable/contractible member is not folded outward being wrapped in the end flap. Therefore, only the corners of the pad-chassis and their peripheries are folded outward and the end flaps are prevented from being folded in large part.

In the preferred embodiment, wherein at least one of the end portions of the second elastically stretchable/contractible members is arranged outward of the corner of the body fluid absorbent core in the longitudinal direction, the second elastically stretchable/contractible member can exert a force in cooperation with the first elastically stretchable/contractible member to fold the corners of the pad-chassis outward by the contractile force thereof.

According to the embodiment, a breast milk absorbent pad is provided which can maintain a curved shape fitted to the shape of the breast while preventing a feeling of discomfort, itchiness, and rash caused by the direct contact of the skin with cut edges formed in the corners of the pad or in a portion of the end flaps during the use.

Though not particularly shown in the drawings, means for folding mentioned above with respect to the pad-chassis can be applied to other articles such as, for example, sanitary napkins and disposable diapers.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The problems which can be solved by the present invention and the effects which can be brought by the present invention are not limited to the problems and the effects explained above. For example, if a certain breast milk absorbent pad conforms to any one of claims, the pad falls in the scope of the present invention, even if the pad cannot solve one of the above problems.

What is claimed is:

1. A breast milk absorbent pad having a longitudinal direction and a transverse direction and comprising:
    a pad-chassis including
    a liquid-pervious inner sheet defining a skin-contactable side,
    a non-liquid-pervious outer sheet defining a non-skin-contactable side, and
    a body fluid absorbent core having a panel shape and interposed between said inner sheet and said outer sheet; and
    first and second elastically stretchable/contractible members respectively extending along transversely opposite sides of said pad-chassis in said longitudinal direction and bonded entirely to said non-liquid-pervious outer sheet in a stretched state and are capable of making said pad-chassis curve in a concave shape with said skin-contactable side inside under a contractible force,
    said first elastically stretchable/contractible members that are arranged outward of transversely opposite side edges of said body fluid absorbent core and extend in said longitudinal direction,
    said second first elastically stretchable/contractible members are attached along said transversely opposite side edges of said body fluid absorbent core in said longitudinal direction extending parallel to said first elastically stretchable/contractible members,
    corners of said pad-chassis which are formed at the intersection of transversely opposite side edges of said pad-chassis extending in said longitudinal direction and longitudinally opposite end edges of said pad-chassis extending in said transverse direction being folded to said non-skin-contactable side, and
    said breast milk absorbent pad being packed in a package with said corners in such a folded state.

2. The breast milk absorbent pad as defined by claim 1, wherein
    said pad-chassis includes
    side flaps arranged transversely outward of transversely opposite side edges of said body fluid absorbent core and extending in said longitudinal direction, and
    end flaps arranged longitudinally outward of longitudinally opposite end edges of said body fluid absorbent core and extending in said transverse direction,
    said corners are located at positions where said side flap joins said end flap, and said first elastically stretchable/contractible members are respectively arranged along said side flaps.

3. The breast milk absorbent pad as defined by claim 1, wherein
    said pad-chassis includes
    side flaps arranged transversely outward of transversely opposite side edges of said body fluid absorbent core and extending in said longitudinal direction, and
    end flaps arranged longitudinally outward of longitudinally opposite end edges of said body fluid absorbent core and extending in said transverse direction,
    said side flaps are, along outermost edge portions of said side flaps, divided into a first portion formed from said inner sheet defining said skin-contactable side, and a second portion formed from said outer sheet and defining said non-skin-contactable side opposite to said first portion, and first elastically stretchable/contractible members are arranged along a lateral edge of said second portions of said side flaps.

4. The breast milk absorbent pad as defined by claim 3, further comprising
    said second elastically stretchable/contractible members are attached to said second portions of said side flaps in a stretched state adjacent said transversely opposite side edges of said body fluid absorbent core and extending parallel to said first elastic stretchable/contractible members, wherein
    of said first and second elastically stretchable/contractible members, at least said second elastically stretchable/contractible members are capable of making said pad-chassis curve in a concave shape with said skin-contactable side inside under a contractile force.

5. The breast milk absorbent pad as defined by claim 3, wherein
    at least one of end portions of said first elastically stretchable/contractible members is arranged outward of a corner of said body fluid absorbent core in said longitudinal direction.

6. The breast milk absorbent pad as defined by claim 3, wherein
    at least one of end portions of said first elastically stretchable/contractible members is arranged inward of a corner of said body fluid absorbent core in said longitudinal direction.

7. The breast milk absorbent pad as defined by claim 4, wherein
    at least one of end portions of said second elastically stretchable/contractible members is arranged outward of said corner of said body fluid absorbent core in said longitudinal direction.

* * * * *